(12) United States Patent
Chun

(10) Patent No.: US 12,257,555 B2
(45) Date of Patent: Mar. 25, 2025

(54) POROUS MEMBRANE FOR SINGLE PARTICLE ANALYSIS

(71) Applicant: KOREA UNIVERSITY RESEARCH AND BUSINESS FOUNDATION, Seoul (KR)

(72) Inventor: Hong Gu Chun, Seoul (KR)

(73) Assignee: Korea University Research and Business Foundation, Seoul (KR)

(*) Notice: Subject to any disclaimer, the term of this patent is extended or adjusted under 35 U.S.C. 154(b) by 952 days.

(21) Appl. No.: 17/414,011

(22) PCT Filed: Dec. 17, 2019

(86) PCT No.: PCT/KR2019/017910
§ 371 (c)(1),
(2) Date: Jan. 6, 2022

(87) PCT Pub. No.: WO2020/130588
PCT Pub. Date: Jun. 25, 2020

(65) Prior Publication Data
US 2022/0126241 A1    Apr. 28, 2022

(30) Foreign Application Priority Data

Dec. 17, 2018 (KR) .................. 10-2018-0163351

(51) Int. Cl.
*B01D 69/02* (2006.01)
*G01N 33/487* (2006.01)
(52) U.S. Cl.
CPC ......... *B01D 69/02* (2013.01); *G01N 33/4875* (2013.01); *B01D 2325/021* (2013.01);
(Continued)

(58) Field of Classification Search
CPC ........ C08J 9/36; B01D 69/02; B01D 2323/02; B01D 2325/38; B01D 2325/36;
(Continued)

(56) References Cited

U.S. PATENT DOCUMENTS 7,022,517 B1 *  4/2006  McDevitt ............... G01N 21/05
                                                      436/524
7,316,899 B2 *  1/2008  McDevitt ........... G01N 21/6452
                                                      977/924

(Continued)

FOREIGN PATENT DOCUMENTS

KR    10-2007-0019723 A    2/2007
KR    10-2017-0089020 A    8/2017

(Continued)

OTHER PUBLICATIONS

Choi, Dong-Hoon, et al. "Fabrication of a Membrane Filter with Controlled Pore Shape and its Application to Cell Separation and Strong Single Cell Trapping," *Journal of Micromechanics and Microengineering*, 25, Oct. 10, 2015 (12 pages in English).

(Continued)

*Primary Examiner* — Shogo Sasaki
(74) *Attorney, Agent, or Firm* — NSIP Law

(57) ABSTRACT

The present invention relates to a porous membrane including a plurality of through-type pores, and when the porous membrane is used, a particle to be analyzed and a reactive particle may be reacted one-to-one, thereby increasing the efficiency and accuracy of particle analysis.

8 Claims, 8 Drawing Sheets

(52) U.S. Cl.
CPC .... *B01D 2325/028* (2013.01); *B01D 2325/36* (2013.01); *B01D 2325/38* (2013.01)

(58) Field of Classification Search
CPC ........ B01D 2325/021; B01D 2325/028; G01N 33/487; G01N 33/4875
See application file for complete search history.

(56) References Cited

U.S. PATENT DOCUMENTS

| | | | | |
|---|---|---|---|---|
| 7,651,868 | B2* | 1/2010 | McDevitt | G01N 33/552 |
| | | | | 422/534 |
| 8,101,431 | B2* | 1/2012 | McDevitt | G01N 21/251 |
| | | | | 436/523 |
| 8,105,849 | B2* | 1/2012 | McDevitt | B01L 3/502738 |
| | | | | 436/523 |
| 8,206,780 | B2* | 6/2012 | Li | B01J 2/22 |
| | | | | 424/490 |
| 8,257,967 | B2* | 9/2012 | McDevitt | G01N 33/54313 |
| | | | | 436/164 |
| 9,102,953 | B2* | 8/2015 | Downey | C12M 21/04 |
| 9,255,472 | B2* | 2/2016 | Downey | C12M 21/04 |
| 9,938,217 | B2* | 4/2018 | Wright | C07C 41/01 |
| 10,385,306 | B2 | 8/2019 | Cho et al. | |
| 2007/0295505 | A1* | 12/2007 | Pfeiffer | C12P 5/023 |
| | | | | 166/263 |
| 2010/0324449 | A1* | 12/2010 | Rostaing | A61B 5/150389 |
| | | | | 600/573 |
| 2012/0078523 | A1* | 3/2012 | Letant | G01N 33/54373 |
| | | | | 435/5 |

FOREIGN PATENT DOCUMENTS

| | | |
|---|---|---|
| KR | 10-2018-0036191 A | 4/2018 |
| KR | 10-2018-0081354 A | 7/2018 |

OTHER PUBLICATIONS

Korean Office Action issued on Apr. 16, 2020 in counterpart Korean Patent Application No. 10-2018-0163351 (3 pages in Korean).
International Search Report issued on May 29, 2020 in counterpart International Patent Application No. PCT/KR2019/017910 (3 pages in English and 4 pages in Korean).
Written Opinion issued on May 29, 2020 in counterpart International Patent Application No. PCT/KR2019/017910 (6 pages in Korean).

* cited by examiner

__(1)__

POROUS MEMBRANE FOR SINGLE PARTICLE ANALYSIS

CROSS REFERENCE TO RELATED APPLICATIONS

This application is a U.S. National Stage Application of International Application No. PCT/KR2019/017910, filed on Dec. 17, 2019, which claims the benefit under 35 USC 119(a) and 365(b) of Korean Patent Application No. 10-2018-0163351, filed on Dec. 17, 2018 in the Korean Intellectual Property Office, the entire disclosure of which is incorporated herein by reference for all purposes.

TECHNICAL FIELD

The present invention relates to a porous membrane including a plurality of through-type pores capable of one-to-one contact between a particle to be analyzed and a reactive particle specifically binding thereto.

BACKGROUND ART

Cells maintain vital phenomena by performing various biological functions such as gene expression, cell growth, cell cycle regulation, metabolic regulation, signal transduction, and the like through various and complex protein-protein interactions.

A cell population research method used for most biological research involves analyzing research results under the assumption that individual cells within a cell population generate a uniform cellular response. However, when the individual cells do not generate the uniform response, analysis of results based on a mean measurement value may be erroneous. Whether or not individual cells actually generate a uniform response is rarely proven experimentally due to technical problems, and thus, technology development for single-cell analysis is essential.

The single-cell analysis is to identify the heterogeneity of individual cells by analyzing genomic characteristics at the single-cell level. As time passes, gene expression of cells may change and apoptosis may even be caused, and thus, the single-cell analysis should be performed rapidly in an environment similar to a biological environment. Representative single-cell analysis methods include a droplet splitting method and a microwell method.

The droplet splitting method is a method of dropping cells and beads to label the cells in a liquid droplet state in a microfluidic channel and arranging them 1:1, and cells with a low concentration are used to prevent two or more cells from entering a single droplet. The microwell method is a method of confining cells and beads one by one in a single microwell and arranging them 1:1, and cells with a low concentration are used to prevent two or more cells from entering a single well. Also, a process of removing a cell doublet by checking with a microscope is required.

In the above two methods, a proportion of including one cell in one droplet or microwell follows the Poisson distribution, and thus, a proportion of arranging cells and beads 1:1 is very low. A proportion of 1:1 arrangement in the droplet method is around 5% and a proportion of 1:1 arrangement in the microwell method is around 10%, and because the proportions of 1:1 arrangement in both methods are very low, two or more cells may be analyzed together. Thus, in order to supplement the existing single-cell analysis methods, a method or apparatus for increasing a proportion of arranging cells and beads 1:1 is required.

DISCLOSURE

Technical Problem

The present invention is directed to providing a porous membrane capable of one-to-one contact between a particle to be analyzed and a reactive molecule specifically binding to the particle to be analyzed.

The present invention is also directed to providing a method of utilizing the porous membrane.

The present invention is also directed to providing an asymmetric porous membrane including a substrate and partition walls formed on the substrate.

Technical Solution

One aspect of the present invention provides
a porous membrane including a plurality of through-type pores,
wherein the pores each include a first pore portion and a second pore portion,
the first pore portion has one end open at one surface of the porous membrane, has a first particle positioned therein, and has a horizontal axis whose minimum length is 0.1 times or more and 1.5 times or less a diameter of the first particle and whose maximum length is 1.0 time or more and 1.9 times or less the diameter of the first particle in a longitudinal section of the first pore portion,
the second pore portion has one end connected to the first pore portion and the other end open at the other surface of the porous membrane, has a second particle specifically reacting with the first particle positioned therein, and has a horizontal axis whose minimum length is 0.1 times or more and 1.5 times or less a diameter of the second particle and whose maximum length is 1.0 time or more and 1.9 or less the diameter of the second particle in a longitudinal section of the second pore portion, and
the first pore portion and the second pore portion have different lengths of the horizontal axes in the longitudinal sections of the pore portions.

Another aspect of the present invention provides
a porous membrane including a plurality of through-type pores,
wherein the pores each include a first pore portion and a second pore portion,
the first pore portion has one end open at one surface of the porous membrane, has a first particle positioned therein, has a horizontal axis whose minimum length is 0.9 times or less a diameter of the first particle in a longitudinal section of the first pore portion, and has a cross-sectional area, which decreases at a certain rate from the one surface of the porous membrane toward the second pore portion, and
the second pore portion has one end connected to the first pore portion and the other end open at the other surface of the porous membrane, has a second particle specifically reacting with the first particle positioned therein, has a horizontal axis whose minimum length is 0.9 times or less a diameter of the second particle in a longitudinal section of the second pore portion, and has the cross-sectional area, which decreases at a certain rate from the other surface of the porous membrane toward the first pore portion.

Still another aspect of the present invention provides a specimen analysis method including: fixing the first particle or the second particle in any one of the pore portions in the porous membrane; and contacting a pore portion in which a particle is fixed with a specimen to be analyzed.

Yet another aspect of the present invention provides a specimen analysis method including: fixing the first particle or the second particle in any one of the pore portions in the porous membrane; sealing the end of a pore portion in which a particle is fixed; and contacting a pore portion in which the particle is not fixed with a specimen to be analyzed.

Yet another aspect of the present invention provides a specimen processing method including: positioning a first particle or a second particle in any one of a first pore portion or a second pore portion in the porous membrane; contacting the particles with a target specimen; and performing suctioning in a pore portion opposite to a pore portion in which the particle is positioned.

Yet another aspect of the present invention provides an asymmetric porous membrane including: a substrate; and partition walls formed in a polygonal or circular pattern on the substrate, wherein a particle is positioned in a space between the partition walls.

Advantageous Effects

When a porous membrane according to an example of the present invention is used, a particle to be analyzed and a reactive particle specifically binding to the particle to be analyzed can be reacted one-to-one, and thus, the efficiency and accuracy of particle analysis can be increased.

MODES OF THE INVENTION

Figure 1:
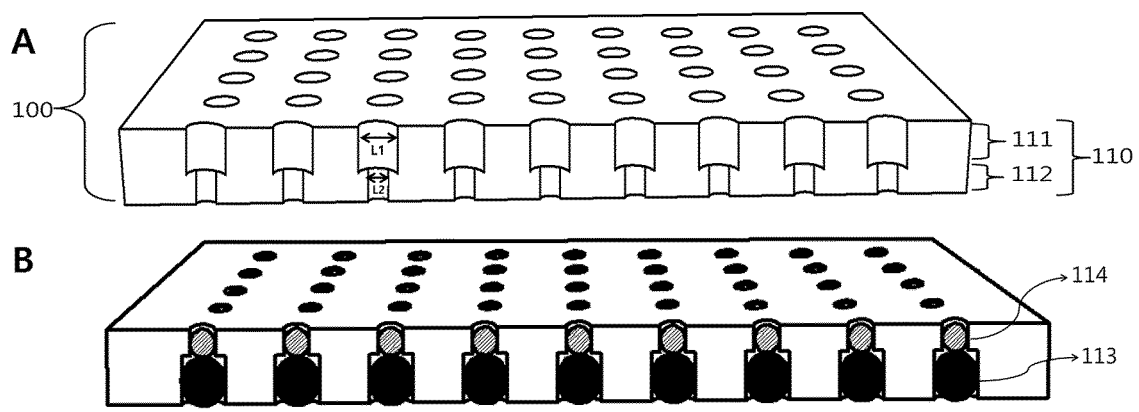
FIG. 1 illustrates a structure of a porous membrane (A) and a state in which a first particle and a second particle are arranged in the porous membrane (B), according to an example of the present invention.

Hereinafter, exemplary embodiments will be described in detail with reference to the accompanying drawings so that one of ordinary skill in the art may readily carry out the present invention. However, in describing exemplary embodiments of the present invention in detail, when it is determined that a detailed description of a related known function or configuration may unnecessarily obscure the gist of the present invention, the detailed description thereof will be omitted. In addition, the same reference numerals are used throughout the drawings for parts having similar functions and functions. Meanwhile, when an element is referred to as "including" or "comprising" another element, unless otherwise stated, the element may further include or comprise still another element rather than preclude the still other element.

FIG. 1 illustrates a structure of a porous membrane (A) and a state in which a first particle and a second particle are arranged in a through-type pore of the porous membrane (B), according to an example of the present invention.

Referring to FIG. 1A, a porous membrane 100 of the present invention may include a plurality of through-type pores 110. The through-type pores 110 each include a first pore portion 111 and a second pore portion 112. The first pore portion 111 has one end open at one surface of the porous membrane 100, and has a horizontal axis whose minimum length of a length L1 may be 0.1 times or more and 1.5 times or less a diameter of a first particle 113 and whose maximum length thereof may be 1.0 time or more and 1.9 times or less the diameter of the first particle 113 in a longitudinal section of the first pore portion 111.

The second pore portion 112 has one end connected to the first pore portion 111 so that the through-type pores 110 may be formed. Also, the other end of the second pore portion 112 is open at the other surface of the porous membrane 100, and has a horizontal axis whose minimum length of a length L2 may be 0.1 times or more and 1.5 times or less a diameter of a second particle 114 and whose maximum length thereof may be 1.0 time or more and 1.9 times or less the diameter of the second particle 114 in a longitudinal section of the second pore portion 112.

When the diameters of the first pore portion 111 and the second pore portion 112 are less than the aforementioned ranges, there may be a problem in that it is difficult for the first particle 113 or the second particle 114 to be located inside the corresponding pore portion. On the other hand, when the diameter of the corresponding pore portion is greater than the aforementioned ranges, a plurality of first particles 113 or second particles 114 are positioned in the corresponding pore portion, thereby hindering the single-particle analysis.

The first pore portion 111 and the second pore portion 112 are spaces in which the first particle 113 and the second particle 114 specifically reacting with the first particle 113 are positioned, respectively, and the first pore portion 111 and the second pore portion 112 may have different lengths L1 and L2 of the horizontal axes, respectively, in the longitudinal sections of the pore portions.

Referring to FIG. 1B, in the porous membrane 100 of the present invention, the first pore portion 111 may have a horizontal axis of a certain length because the minimum length of the horizontal axis and the maximum length of the horizontal axis are equal to each other in the longitudinal section of the first pore portion 111, and the certain length may be 1.0 time or more and 1.5 times or less the diameter of the first particle 113. Also, the second pore portion 112 may have a horizontal axis of a certain length because the minimum length of the horizontal axis and the maximum length of the horizontal axis are equal to each other in the longitudinal section of the second pore portion 112, the certain length may be 1.0 time or more and 1.5 times or less the diameter of the second particle 114, and the diameter of the first particle 113 may be greater than that of the second particle 114.

Figure 2:
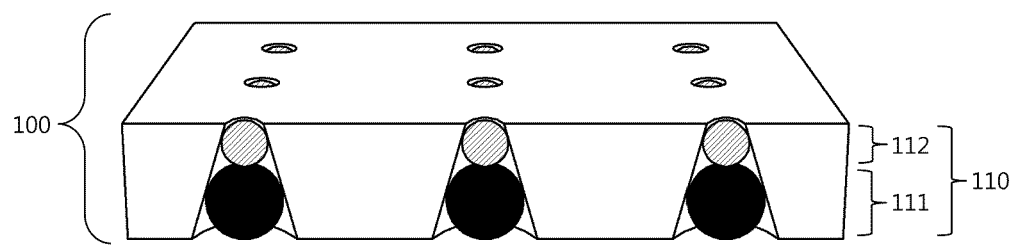
FIG. 2 illustrates an example of a porous membrane having truncated cone-shaped through-type pores.
Figure 3:
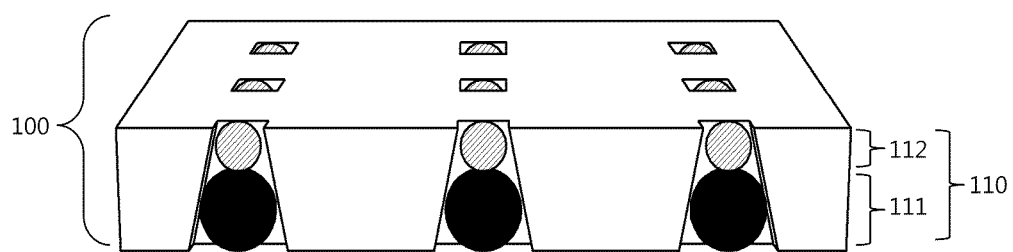
FIG. 3 illustrates an example of a porous membrane having truncated quadrangular pyramid-shaped through-type pores.

FIGS. 2 and 3 illustrate an example of a porous membrane having truncated cone-shaped or truncated quadrangular pyramid-shaped through-type pores.

As used herein, the term "truncated cone" refers to a portion that is not a cone in a three-dimensional figure created by cutting a cone with a plane parallel to the base, and the term "truncated quadrangular pyramid" refers to a portion that is not a quadrangular pyramid in a three-dimensional figure created by cutting a quadrangular pyramid with a plane parallel to the base.

In the porous membrane 100 having truncated cone-shaped or truncated quadrangular pyramid-shaped through-type pores, the first pore portion 111 has a horizontal axis L1 whose minimum length is 0.5 times or more and 1.2 times or less a diameter of a first particle and whose maximum length is 1.0 time or more and 1.5 times or less the diameter of the first particle in a longitudinal section of the first pore portion, and the second pore portion 112 has a horizontal axis L2 whose minimum length is 0.5 times or more and 1.2 times or less a diameter of a second particle and whose maximum length is 1.0 time or more and 1.5 times or less the diameter of the second particle in a longitudinal section of the second pore portion. Also, the maximum length of the horizontal axis in the longitudinal section of the first pore portion 111 and the minimum length of the horizontal axis in the longitudinal section of the second pore portion 112 may be equal to each other.

In the present invention, in the porous membrane, the shapes of the longitudinal sections of the first pore portion 111 and the second pore portion 112 may be asymmetric. For example, the longitudinal section of the first pore portion 111 may be rectangular and the longitudinal section of the second pore portion 112 may be rhombic, or the longitudinal section of the first pore portion 111 may be rectangular and the longitudinal section of the second pore portion 112 may have a rectangular shape having a size smaller than that of the longitudinal section of the first pore portion 111. Due to this asymmetry, a first particle and a second particle may be respectively positioned in the pore portions.

Figure 4:
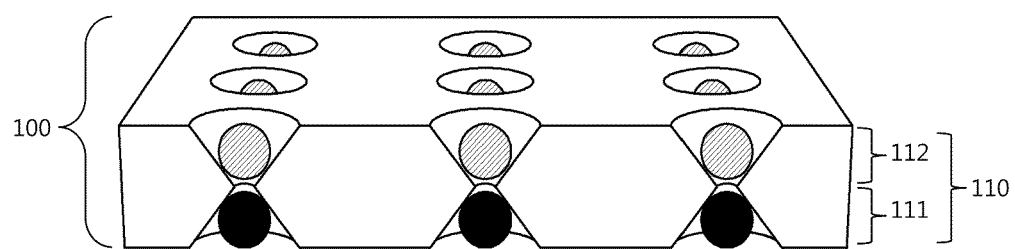
FIG. 4 illustrates an example of a porous membrane having through-type pores in which a first pore portion and a second pore portion are symmetrical.

FIG. 4 illustrates an example of the porous membrane 100 having the through-type pores 110 in which the first pore portion 111 and the second pore portion 112 are symmetrical.

In the porous membrane 100 shown in FIG. 4, the through-type pores 110 each include the first pore portion 111 and the second pore portion 112 that are vertically symmetrical. The first pore portion 111 has one end open at one surface of the porous membrane 100, has a first particle positioned therein, has a horizontal axis whose minimum length is 0.9 times or less a diameter of the first particle in a longitudinal section of the first pore portion 111, and may have a cross-sectional area, which may decrease at a certain rate from the one surface of the porous membrane 100 toward the second pore portion 112.

Also, the second pore portion 112 has one end connected to the first pore portion 111 and the other end open at the other surface of the porous membrane 100, has a second particle, which specifically reacts with the first particle, positioned therein, has a horizontal axis whose minimum length is 0.9 times or less a diameter of the second particle in a longitudinal section of the second pore portion 112, and may have a cross-sectional area, which may decrease at a certain rate from the other surface of the porous membrane 100 toward the first pore portion 111.

In the porous membrane 100 shown in FIG. 4, the first pore portion 111 and second pore portion 112 may be connected to each other to form a truncated cone-shaped through-type pore or a truncated quadrangular pyramid-shaped through-type pore.

Also, in the porous membrane 100 shown in FIG. 4, the first pore portion 111 has a horizontal axis whose minimum length is 0.1 times or more and 0.9 times or less the diameter of the first particle and whose maximum length is 1 time or more and 5 times or less the diameter of the first particle in the longitudinal section of the first pore portion 111, and the second pore portion 112 has a horizontal axis whose minimum length is 0.1 times or more and 0.9 times or less the diameter of the second particle and whose maximum length is 1 time or more and 5 times or less the diameter of the second particle in the longitudinal section of the second pore portion 112.

In the present invention, the first particle and the second particle may each be a bead or a cell, and when the cell is dissolved, nucleic acids, lipids, saccharides, antibodies, enzymes, and hormones are also included in the particles of the present invention. The bead may be, but is not limited to, polystyrene beads, metal nanobeads, or the like, and may be a bead whose surface is modified with antibodies, fluorescent molecules, or the like. Also, the particles may be cells, nucleic acids, lipids, saccharides, antibodies, enzymes, and hormones isolated from a biological sample.

The through-type pores 110 are arranged at regular intervals in the porous membrane 100 shown in FIGS. 1 to 4 of the present invention, and when the number of pores is too small, an amount of particles to be analyzed, which are positioned in a pore portion, is too small, and thus analysis efficiency may decrease.

Also, in the porous membrane 100 shown in FIGS. 1 to 4, interiors of a first pore portion and a second pore portion may be coated with a hydrophilic material in order to prevent diffusion or dispersion of a first particle and a second particle, and the remaining portion except for the interiors may be coated with a hydrophobic material. In contrast, interiors of the first pore portion and the second pore portion may be coated with a hydrophobic material, and the remaining portion except for the interiors may be coated with a hydrophilic material. Also, by considering a material of a porous membrane, an interior of a pore portion may be coated with a material having characteristics opposite to those of the material. The hydrophilic material that may be coated on the first pore portion and the second pore portion includes silicon, and the hydrophobic material includes polydimethylsiloxane.

In the present invention, the porous membrane 100 may include, but is not limited to, a material selected from the group consisting of silicon, polydimethylsiloxane (PDMS), polyethersulfone (PES), polymethyl methacrylate (PMMA), polystyrene (PS), polyurethane acrylate (PUA), and polycarbonate (PC).

Figure 5:
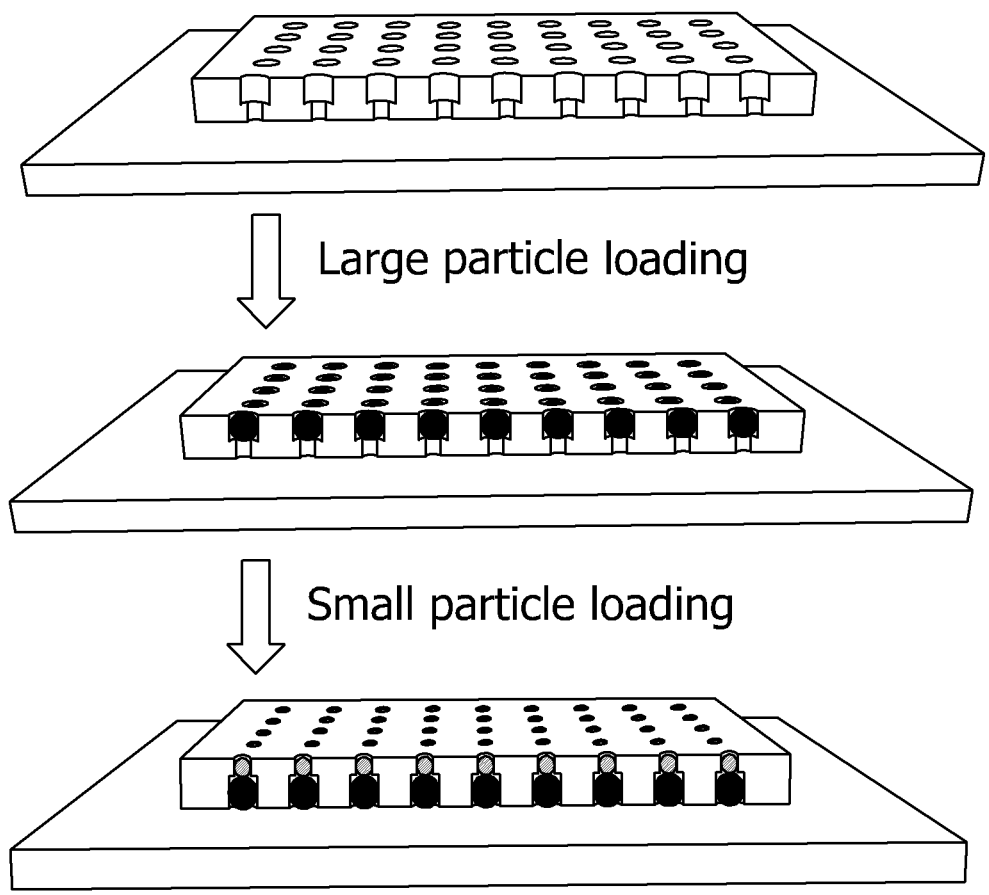
FIG. 5 illustrates a method of arranging a first particle and a second particle one-to-one in a porous membrane of the present invention.

FIG. 5 shows a method of arranging a first particle and a second particle one-to-one in a porous membrane of the present invention.

First, when the first particle 113 is fixed in the first pore portion 111 of the porous membrane 100, the porous membrane 100 is inverted, and then the second particle 114 is fixed in the second pore portion 112, the first particle 113 and the second particle 114 are in one-to-one contact. The first particle 113 and the second particle 114 may each be a bead or a cell.

Figure 6:
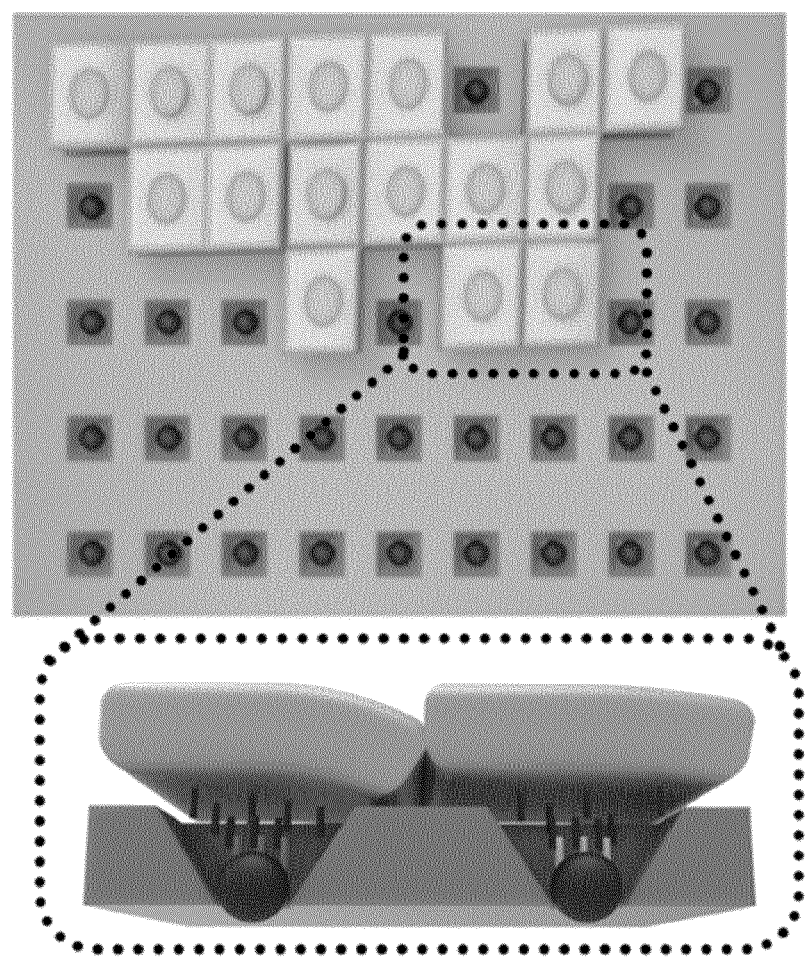
FIG. 6 schematically illustrates a process of fixing particles in a porous membrane of the present invention and then contacting the particles with tissue sections.

FIG. 6 shows a process of fixing particles in a porous membrane of the present invention and then contacting the particles with tissue sections.

In detail, the present invention provides a specimen analysis method including: (a) fixing a first particle or a second particle in any one of pore portions in a porous membrane; and (b) contacting a pore portion in which a particle is fixed with a specimen to be analyzed.

Also, the present invention provides a specimen analysis method including: (a) fixing a first particle or a second particle in any one of pore portions in a porous membrane; (b) sealing the end of a pore portion in which a particle is fixed; and (c) contacting a pore portion in which the particle is not fixed with a specimen to be analyzed.

In the present invention, the sealing of (b) may include a method of closing the end of the pore portion with a material selected from the group consisting of polydimethylsiloxane, hydrogel, agarose, an oil, tape, a glass plate, a quartz plate, a silicon plate, polycarbonate, and anodized aluminum oxide.

Also, the specimen to be analyzed may be selected from the group consisting of a tissue section, a body fluid, a cell, and a cell lysate isolated from a living body.

The first particle and the second particle may each be a bead or a cell, as described above in the present specification.

Figure 7:
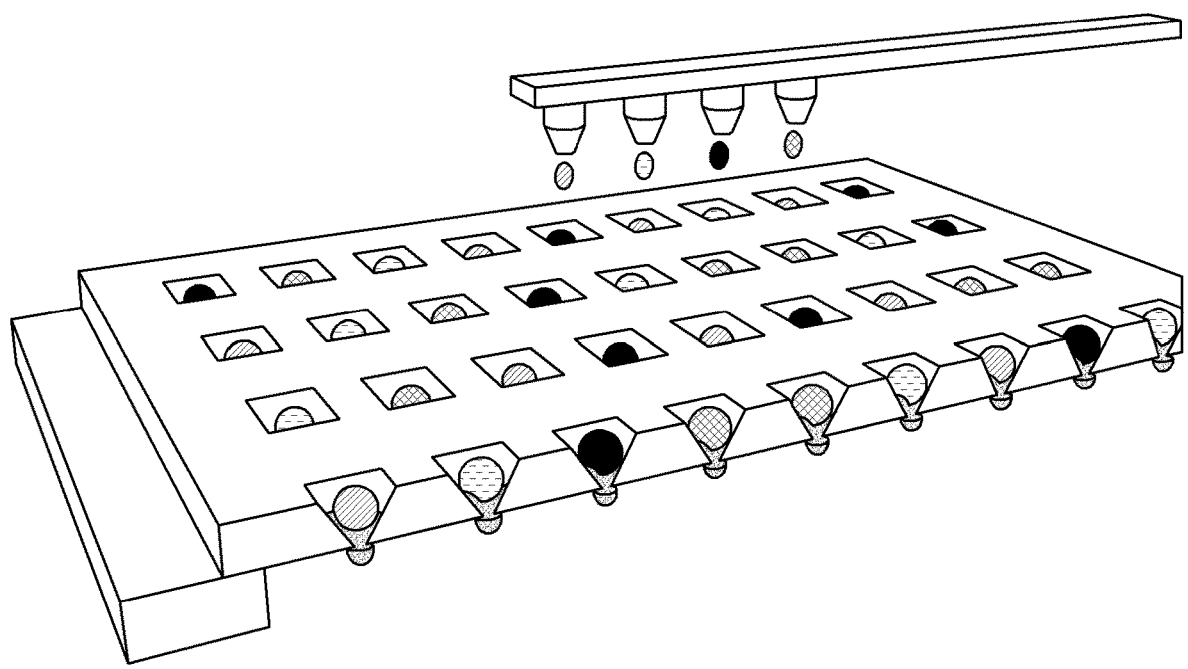
FIG. 7 schematically illustrates a process of arranging a single particle in a porous membrane of the present invention and performing suctioning by dispensing a target specimen.

FIG. 7 shows a process of arranging a single particle in a porous membrane and performing suctioning by dispensing a target specimen.

In detail, the present invention provides a specimen processing method including: (a) positioning a first particle or a second particle in any one of a first pore portion or a second pore portion in a porous membrane; (b) contacting each of a particle with a target specimen; and (c) performing suctioning in a pore portion opposite to a pore portion in which the particle is positioned.

In the present invention, the target specimen of (b) may include the group consisting of adenine, adenine derivatives, guanine, guanine derivatives, cytosine, cytosine derivatives, thymine, thymine derivatives, and mixtures thereof. Also, the target specimen of (b) may include a catalytic material capable of accelerating the reaction of a material such as the adenine.

In the present invention, the specimen processing method may be utilized for nucleic acid synthesis, for example, a DNA oligomer synthesis method. In a conventional DNA synthesis method using a plate microarray, a process of selectively adding A, G, T and C to each spot on a plate and washing them is repeated. However, because the washing proceeds in a horizontal direction of the plate, there is a possibility that a solution that has not reacted at one spot flows sideways and reacts at another spot. Also, when a washing solution flows sideways, a laminar flow is formed, and a flow rate becomes slower as it approaches a surface of the plate, and thus, washing efficiency in a region near the surface of the plate where DNA is being synthesized decreases. Thus, the washing while dropping the washing solution sideways on the plate is inefficient.

In contrast, when the porous membrane 100 of the present invention is used, nucleic acid hexane may be efficiently synthesized through positioning a nucleic acid-fixing bead in a first pore portion or a second pore portion of the porous membrane 100, contacting the nucleic acid-fixing bead with adenine, adenine derivatives, guanine, guanine derivatives, cytosine, cytosine derivatives, thymine, thymine derivatives, or mixtures thereof, and washing the first pore portion or the second pore portion.

The washing may be performed by adding a washing solution to the first pore portion and then performing suctioning in the second pore portion, or vice versa. Because the washing is performed in a vertical direction, materials that are not used for DNA synthesis escape to the bottom of the porous membrane 100, and unwanted contamination of nucleic acid molecules may be prevented.

Figure 8:
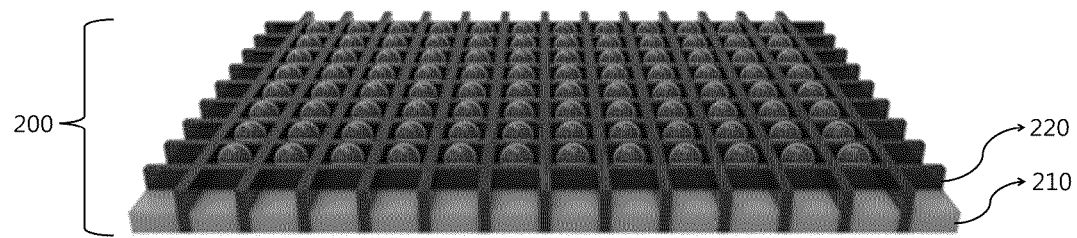
FIG. 8 illustrates an example of an asymmetric porous membrane in which a pattern is formed on a surface of a substrate.

FIG. 8 shows an example of an asymmetric porous membrane in which a pattern is formed on a surface of a substrate.

In detail, the present invention provides an asymmetric porous membrane including: a substrate; and partition walls formed in a polygonal or circular pattern on the substrate, wherein a particle is positioned in a space between the partition walls.

In the present invention, the substrate may be made of a material selected from the group consisting of paper, cellulose, cellulose derivatives, and glass fiber, and the partition walls may be made of a material such as wax, a polymer, or a photoresist.

Because paper has a fine porous structure, when the partition walls are formed on a paper substrate, relatively large pores are formed on one side by the partition walls and fine pores are formed on the paper substrate side, resulting in the formation of an asymmetric porous structure on the paper substrate.

As used herein, the term "photoresist" refers to a material whose physical properties change when exposed to light (mainly ultraviolet), and includes a negative photoresist and a positive photoresist, wherein when the negative photoresist is exposed to light, a reaction such as crosslinking occurs, resulting in a significant increase in molecular weight and a decrease in solubility, and when the positive photoresist is exposed to light, solubility increases by reactions such as decomposition and branched chain cleavage. When the positive photoresist is deposited on the substrate, a mask of a desired pattern is placed thereon, and then light is irradiated, the portion exposed to the light is dissolved and only the photoresist corresponding to the pattern of the mask remains, and thus partition walls may be formed on the substrate.

Hereinbefore, the present invention has been described in detail using exemplary embodiments, but the scope of the present invention is not limited to specific embodiments, and those of ordinary skill in the art to which the present invention pertains will understand that the present invention may be implemented in a modified form without departing from the essential characteristics of the present invention. Therefore, the embodiments should be considered in a descriptive sense only and not for purposes of limitation. The scope of the present invention is defined not by the detailed descriptions of the present invention but by the following claims, and all differences within the scope will be construed as being included in the present invention.

The invention claimed is:
1. A porous membrane comprising:
a first surface and a second surface; and
a plurality of through pores,
wherein each of the plurality of through pores comprises a first pore portion and a second pore portion,
wherein the first pore portion has one end open at the first surface of the porous membrane, has a first particle positioned therein, and has a horizontal axis of a minimum length of 0.1 times or more and 1.5 times or less than a diameter of the first particle and of a maximum length of 1.0 times or more and 1.9 times or less than the diameter of the first particle in a longitudinal section of the first pore portion, wherein the second pore portion has one end connected to the first pore portion and another end open at the second surface of the porous membrane, has a second particle, which specifically reacts with the first particle, positioned therein, and has a horizontal axis of a minimum length of 0.1 times or more and 1.5 times or less than a diameter of the second particle and of a maximum length of 1.0 times or more and 1.9 times or less than the diameter of the second particle in a longitudinal section of the second pore portion, and wherein the horizontal axis of the first pore portion and the horizontal axis of the second pore portion have different lengths from each other in the longitudinal section of the first pore portion and the longitudinal section of the second pore portion.

2. The porous membrane of claim 1, wherein the first pore portion has the horizontal axis of a set length such that the minimum length of the horizontal axis and the maximum length of the horizontal axis are equal to each other in the longitudinal section of the first pore portion, and the set length is 1.0 times or more and 1.5 times or less than the diameter of the first particle, and wherein the second pore portion has the horizontal axis of a set length such that the minimum length of the horizontal axis and the maximum length of the horizontal axis are equal to each other in the longitudinal section of the second pore portion, and the set length is 1.0 times or more and 1.5 times or less than the diameter of the second particle, and wherein the diameter of the first particle is greater than the diameter of the second particle.

3. The porous membrane of claim 1, wherein the first pore portion has the horizontal axis of a minimum length of 0.5 times or more and 1.2 times or less than the diameter of the first particle and of a maximum length of 1.0 times or more and 1.5 times or less than the diameter of the first particle in the longitudinal section of the first pore portion, wherein the second pore portion has the horizontal axis of a minimum length of 0.5 times or more and 1.2 times or less than the diameter of the second particle and of a maximum length of 1.0 times or more and 1.5 times or less than the diameter of the second particle in the longitudinal section of the second pore portion, and wherein the maximum length of the horizontal axis in the longitudinal section of the first pore portion and the minimum length of the horizontal axis in the longitudinal section of the second pore portion are equal to each other.

4. The porous membrane of claim 1, wherein shapes of the longitudinal sections of the first pore portion and the second pore portion are asymmetric.

5. The porous membrane of claim 1, wherein the through pores are arranged at regular intervals.

6. The porous membrane of claim 1, wherein each of the first particle and the second particle are each a bead or a cell.

7. The porous membrane of claim 1, wherein interiors of the first pore portion and the second pore portion are coated with a hydrophilic material, and exteriors of the first pore portion and the second pore portion are coated with a hydrophobic material.

8. The porous membrane of claim 1, wherein interiors of the first pore portion and the second pore portion are coated with a hydrophobic material, and exteriors of the first pore portion and the second pore portion are coated with a hydrophilic material.

* * * * *